United States Patent [19]

Sarantakis

[11] 4,221,682
[45] Sep. 9, 1980

[54] TETRAPEPTIDES HAVING ANALGESIC ACTIVITY

[75] Inventor: Dimitrios Sarantakis, West Chester, Pa.

[73] Assignee: American Home Products Corporation, New York, N.Y.

[21] Appl. No.: 64,159

[22] Filed: Aug. 6, 1979

[51] Int. Cl.$^2$ .................. C08L 37/00; C07C 103/52; A61K 37/00
[52] U.S. Cl. .............................. 260/8; 260/112.5 R; 424/177
[58] Field of Search .......................... 260/112.5 R, 8; 424/177

[56] References Cited

U.S. PATENT DOCUMENTS 4,148,786   4/1979   Sarantakis .................. 260/112.5 R

FOREIGN PATENT DOCUMENTS 850776   7/1977   Belgium ........................... 260/112.5 R
857138   1/1978   Belgium ........................... 260/112.5 R

*Primary Examiner*—Delbert R. Phillips
*Attorney, Agent, or Firm*—George Tarnowski

[57] ABSTRACT

The polypeptides of the formula:

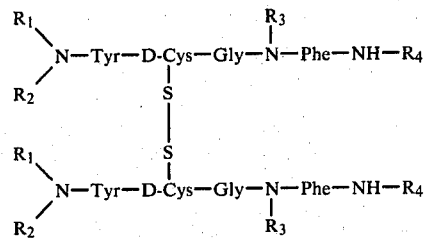

wherein
  $R_1$ is hydrogen or lower alkyl;
  $R_2$ is hydrogen, lower alkyl, allyl, 2-methylpropenyl, cyclopropylmethyl or cyclobutylmethyl;
  $R_3$ is hydrogen or lower alkyl; and
  $R_4$ is hydrogen, lower alkyl or hydroxy lower alkyl;

the monomeric precursors thereof or a pharmacologically acceptable salt thereof, exert an analgesic effect in warm-blooded animals when peripherally administered.

4 Claims, No Drawings

TETRAPEPTIDES HAVING ANALGESIC ACTIVITY

BACKGROUND OF THE INVENTION

Enkephalin, a natural opiate receptor agonist in the brain, has been identified [see Hughes et al., Nature, 256, 557 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates. It has been reported that methionine-enkephalin and leucine-enkephalin, when administered by injection in the brain ventricle in rats, induce a profound analgesia that is fully reversible by naloxone. [See Beluzzi et al., Nature, 260, 625(1976)]. The enkephalins are inactive when administered peripherally, however, and it is believed that the enkephalins are rapidly destroyed by blood enzymes and/or are poorly transported across the bloodbrain barrier.

Various structural modifications of methionine-enkephalin and leucine-enkephalin are described in the literature. For example, H-Tyr-D-Ala-Gly-Phe-Met-$NH_2$ has been reported by Pert et al., Nature 262, 738(1976) to produce long lasting analgesic after central administration. Bajusz et al., Acta. Biochem. Biophys. Acta. Sci. Hung., 11, 305(1976) report peripheral (i.v.) analgesic activity in rats for H-Tyr-D-Met-Gly-Phe-Pro-$NH_2$. Fredrickson, Life Sciences, 21, 23(1977) reported H-Tyr-D-Ala-Gly-Phe-D-Met-$NH_2$ produced analgesic activity in rats when centrally administered. The pentapeptide, H-Tyr-D-Ala-Gly-Phe-D-Leu-OH was shown by Baxter et al., Proc. of the B.P.S. page 456(1977) to exhibit antinociceptive and behavioral effects in both rats and mice after central administration and by Wei et al., Life Sciences, 21, 321(1977) to exhibit peripheral analgesic activity. Romer et al., Nature, 268, 547(1977) has shown that the polypeptide amide

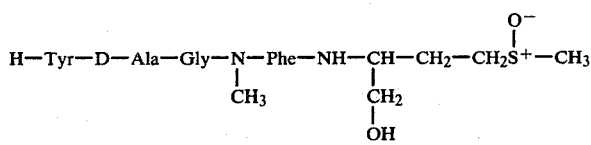

possesses potent peripheral analgesic activity and some analgesic activity when given orally at high doses.

The present invention relates to novel synthetic tetrapeptides which produce an analgesic effect in warm-blooded animals upon peripheral administration.

DESCRIPTION OF THE INVENTION

The invention comprises a group of analgesic polypeptides of the formula:

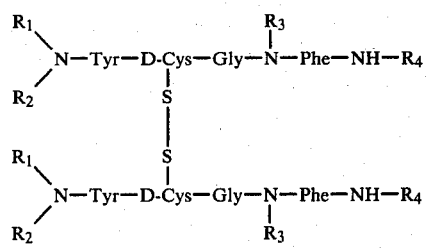

wherein $R_1$ is hydrogen or lower alkyl; $R_2$ is hydrogen, lower alkyl, allyl, 2-methyl-propenyl, cyclopropylmethyl or cyclobutylmethyl; $R_3$ is hydrogen or lower alkyl; and $R_4$ is hydrogen, lower alkyl or hydroxy lower alkyl; the monomeric precursor thereof or a pharmaceutically acceptable salt thereof, which exert an analgesic effect in warm-blooded animals when peripherally administered.

The term "lower alkyl" as used herein, refers to straight and branched chain hydrocarbon radicals containing from 1 to about 6 carbon atoms.

The monomeric precursors of the disulfide polypeptides depicted above, which may be in the form of pharmaceutically acceptable salts, may be represented by the general formula

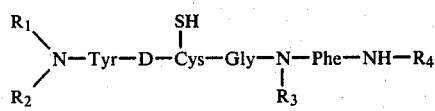

wherein $R_1$, $R_2$, $R_3$, and $R_4$ are the same as described hereinbefore.

All chiral amino acid residues depicted in the preceding structural formulas and elsewhere throughout the disclosure and the appended claims are in the natural or L-configuration except the indicated D-Cys is 2-position.

The pharmaceutically acceptable salts of the polypeptides of this invention are acid addition salts of the free base in which the acid may be either organic or inorganic, as for example, hydrochloric, phosphoric,, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by typical solid phase procedures employing a benzhydrylamine polystyrene based resin for the production of the C-terminal amides. The polypeptide is removed from the resin support with HF and purified by gel filtration.

The N-substituted tyrosine and phenylalanine derivatives employed in 1- and 4-positions of the polypeptide are prepared as reactants by reaction of methylchloride, allylchloride, cyclopropylmethyl chloride, etc. with a Boc protected ester of the appropriate amino acid in the presence of silver oxide. The product is then saponified and hydrolyzed to obtain the desired reactant.

The following examples illustrate the preparation of the polypeptides of the invention.

EXAMPLE 1 tert-Butyloxycarbonyl-0-2,6-dichlorobenzyl-L-tyrosyl-S-p-methoxybenzyl-D-cysteinyl-glycyl-N-methyl-L-phenylalanyl-benzhydrylamine polystyrene resin 8 g. of benzhydrylamine polystyrene resin hydrochloride (Bachem Inc.) containing approximately 0.6 mmoles/g. of free amino groups, is placed in the reaction vessel of a Beckman 990A peptide synthesizer and subjected to subsequent cycles of amino group deprotections and amino acid couplings as described in programs 1 and 2, the latter being performed to secure complete coupling of each amino acid. The following amino acids are incorporated onto the benzhydrylamine resin: Boc-N-Me-Phe-OH, Boc-Gly-OH, Boc-D-Cys(SMBzl)OH and Boc-Tyr(Cl$_2$Bzl)OH to yield the title peptidoresin.

PROGRAM 1

1. Wash with $CH_2Cl_2 \times 3$.
2. Treat with TFA-$CH_2Cl_2$-EDT, (1:1:5%, v/v for 5 min.)
3. Treat as in 2 for 25 minutes.
4. Wash with $CH_2Cl_2 \times 4$.
5. Treat with TEA 12% in DMF for 1 minute.
6. Treat as in 5 for 5 minutes.
7. Wash with $CH_2Cl_2 \times 3$.
8. Add 4 equivalents of Boc-protected amino acid and stir for 5 min.
9. Add 2 equivalents of 1 M-DIC solution in DMF and stir for 25 min.
10. Add 2 equivalents of 1 M-DIC solution in DMF and stir for 180 mins.
11. Wash with $CH_2Cl_2 \times 3$.
12. Wash with methanol $\times 3$.
13. Wash with $CH_2Cl_2 \times 3$.

Program 2

1. Wash with $CH_2Cl_2 \times 3$.
2. Add 2 equivalents of Boc-protected amino acid and stir for 5 min.
3. Add 2 equivalents of 1 M-DIC solution in DMF and stir for 180 mins.
4. Wash with DMF $\times 3$.
5. Wash with $CH_2Cl_2 \times 3$.
6. Wash with methanol $\times 3$.
7. Wash with $CH_2Cl_2 \times 3$.

EXAMPLE 2

L-Tyrosyl-D-Cysteinyl-Glycyl-N-Methyl-L-Phenylalanyl Amide Disulfide Acetate

The peptidoresin of the previous example (about 10 g.) is mixed with 15 ml. anisole and is treated with 150 ml. liquid HF for 60 minutes at 18° C. in the absence of air. The excess HF is evaporated as rapidly as possible in vacuo and the residue is extracted with 20% aqueous acetic acid and filtered. The filtrate is treated with Bio Rad AG3-X4 resin (in the chloride form) for 30 minutes and then lyophilized to yield a white solid. The latter is dissolved in 100 ml. of 5% aqueous acetic acid and the pH is adjusted to 7.6 with dilute NH$_4$OH and stirred overnight. The pH is subsequently adjusted to 5 with glacial acetic acid and lyophilized to yield an off-white solid. This solid is chromatographed through a column of Sephadex G-10 (2.5×80 cm.) and eluted with 10% aqueous acetic acid. The fractions (each fraction 5.5 μl.) in tubes 58 to 72 are pooled and lyophilized to yield 79 mg. of the title compound.

TLC, silica gel precoated glass plates, Merck, Rf (n-butanol-water-acetic acid, 4:1:1, v/v) 0.5.

TLC, cellulose precoated glass plates, Merck, Rf (n-butanol-water-acetic acid, 4:1:1, v/v) 0.7.

Amino acid analysis: Gly (1) 1, Tyr (1) 1.5, NH$_3$ (1) 1.22.

The analgesic activity of the polypeptides of this invention is demonstrated by the standard rat-tail flick test of D'Amour and Smith, J. Pharmacol. Exp. Ther., 72, 74(1941), whereby groups of six male rats (150–200 gms.) are placed in individual holders. The holders are situated so that a high intensity light beam will shine on the tip of the rats tail. The light beam intensity is adjusted so that normal rats respond by removing their tails from the light stimulus within from 3 to 8 seconds. The average of three time readings for removal of a rats tail from the light beam, taken 20 minutes apart serves as a pre-drug control. The rats are selected for use based upon control readings that agree within one second. The compounds of this invention are then administered intravenously and the test performed at 15, 30 and 60 minutes to determine the animals reaction time which is compared with the control average and tested for significance. The number of rats showing analgesia at each time period out of the total group for each dose administered is noted as a ratio and the number of positive responses observed is relative to the total number of challenges for each group of rats. The results are summarized in the following table:

| Compound | Dose (mg/kg) | Time (minutes) No. Analgesic/ No. Tested | | | Positive Responses Total Possible Response | Comments |
|---|---|---|---|---|---|---|
| | | 15 | 30 | 60 | | |
| Example 2 | 5.0 i.v. | 6/6 | 5/6 | 5/6 | 16/18 | 6/6 Respiration very depressed 0/6 dead |
| Example 2 | 1.0 i.v. | 3/6 | 2/6 | 1/5 | 6/17 | 5/5 Respiration normal 1/6 dead |

The test results demonstrate that the compounds of this invention induce analgesia upon administration of a single intravenous injection at a dose as low as 1.0 milligram per kilogram. For practical purposes, it is contemplated, based upon the proceding test results, that a dose of from about 1.0 to about 5 milligrams per kilogram in single or plural doses is the appropriate dosage to achieve that degree of analgesia desired for various applications. The exact dose to be employed will, of course, vary with the specific compound employed, the patient and the degree of analgesia desired. The determination of a precise dose for production of a desired effect is readily determined empirically by the physician.

The protected intermediates for monomeric precursors and the dimeric polypeptides disclosed herein form an additional aspect of the invention. The intermediates are of the formula:

$$\begin{array}{c} \phantom{\diagdown}\text{F}\phantom{\diagup}\phantom{xx}\text{D}\\ \phantom{\diagdown}|\phantom{xxxx}|\\ \text{A}\phantom{\diagdown}\phantom{x}\text{O}\phantom{xx}\text{S}\\ \phantom{x}\diagdown\phantom{x}|\phantom{xxxx}|\\ \phantom{xxxx}\text{N—Tyr—D-Cys—Gly—N—Phe—NH-(resin support)}\\ \phantom{x}\diagup\phantom{xxxxxxxxxxxxxx}|\\ \text{R}_1\phantom{xxxxxxxxxxxxx}\text{R}_3 \end{array}$$

in which $R_1$ and $R_3$ are as defined hereinbefore;

A is hydrogen or an α-amino protecting group;

F is a protecting group for the phenolic hydroxy group of tyrosyl; and

D is a protecting group for the mercapto group of D-cysteinyl.

Of the many protecting groups known to the art for use in conjunction with each of the functional groups found in the depicted polypeptide intermediate, the most preferred are tert-butyloxycarbonyl (Boc) for the α-amino group of the tyrosyl moiety, 2,6-dichlorobenzyl (Cl$_2$Bzl) for the phenolic hydroxyl group of the tyrosyl moiety and p-methoxybenzyl (MBzl) for the mercapto group of the D-cysteinyl moiety and the C-terminal moiety.

What is claimed is:

1. A polypeptide of the formula:

$$\begin{array}{c}\text{R}_1\phantom{xxxxxxxxxxxxxx}\text{R}_3\\ \phantom{x}\diagdown\phantom{xxxxxxxxxxxx}|\\ \phantom{xxxx}\text{N—Tyr—D-Cys—Gly—N—Phe—NH—R}_4\\ \phantom{x}\diagup\phantom{xxxxxxxxxxx}|\\ \text{R}_2\phantom{xxxxxxxxxxxxx}\text{S}\\ \phantom{xxxxxxxxxxxxxxxx}|\\ \phantom{xxxxxxxxxxxxxxxx}\text{S}\\ \text{R}_1\phantom{xxxxxxxxxxxxx}|\\ \phantom{x}\diagdown\phantom{xxxxxxxxxxx}\\ \phantom{xxxx}\text{N—Tyr—D-Cys—Gly—N—Phe—NH—R}_4\\ \phantom{x}\diagup\phantom{xxxxxxxxxxx}|\\ \text{R}_2\phantom{xxxxxxxxxxxxx}\text{R}_3 \end{array}$$

wherein $R_1$ is hydrogen or lower alkyl;

$R_2$ is hydrogen, lower alkyl, allyl, 2-methylpropenyl, cyclopropylmethyl or cyclobutylmethyl;

$R_3$ is hydrogen or lower alkyl; and $R_4$ is hydrogen, lower alkyl or hydroxy lower alkyl; the monomeric precursor thereof or a pharmaceutically acceptable salt thereof.

2. A compound of claim 1, which is Tyr-D-Cys-Gly-N-methyl-Phe-NH$_2$ disulfide, its monomeric precursor or a pharmaceutically acceptable salt thereof.

3. A compound of the formula:

$$\begin{array}{c} \phantom{\diagdown}\text{F}\phantom{\diagup}\phantom{xx}\text{D}\\ \phantom{\diagdown}|\phantom{xxxx}|\\ \text{A}\phantom{\diagdown}\phantom{x}\text{O}\phantom{xx}\text{S}\\ \phantom{x}\diagdown\phantom{x}|\phantom{xxxx}|\\ \phantom{xxxx}\text{N—Tyr—D-Cys—Gly—N—Phe—NH-(resin support)}\\ \phantom{x}\diagup\phantom{xxxxxxxxxxxxxx}|\\ \text{R}_1\phantom{xxxxxxxxxxxxx}\text{R}_3 \end{array}$$

wherein $R_1$ is hydrogen or lower alkyl;

$R_3$ is hydrogen or lower alkyl;

A is hydrogen or an α-amino protecting group;

F is a phenolic protecting group; and

D is a mercapto protecting group.

4. A compound of claim 3 in which A is tert-butylcarbonyl, F is 2,6-dichlorobenzyl and D is p-methoxybenzyl.

* * * * *